(12) United States Patent
Ikeda

(10) Patent No.: US 8,409,078 B2
(45) Date of Patent: Apr. 2, 2013

(54) ENDOSCOPE

(75) Inventor: Toshiyuki Ikeda, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 867 days.

(21) Appl. No.: 11/783,843

(22) Filed: Apr. 12, 2007

(65) Prior Publication Data

US 2007/0244360 A1    Oct. 18, 2007

(30) Foreign Application Priority Data

Apr. 13, 2006    (JP) ................................ 2006-110956

(51) Int. Cl.
*A61B 1/04*    (2006.01)
(52) U.S. Cl. ........................ 600/116; 600/115; 600/121
(58) Field of Classification Search .......... 600/115–116, 600/120–125, 127, 129, 139–152; 604/96.01, 604/101.01, 101.04, 103.05
See application file for complete search history.

(56) References Cited

U.S. PATENT DOCUMENTS

| | | | | |
|---|---|---|---|---|
| 4,040,413 A | * | 8/1977 | Ohshiro | 600/116 |
| 4,148,307 A | * | 4/1979 | Utsugi | 600/116 |
| 4,224,929 A | * | 9/1980 | Furihata | 600/116 |
| 4,911,163 A | * | 3/1990 | Fina | 606/127 |
| 5,398,670 A | * | 3/1995 | Ortiz et al. | 600/114 |
| 6,007,482 A | * | 12/1999 | Madni et al. | 600/115 |
| 6,126,635 A | * | 10/2000 | Simpson et al. | 604/101.05 |
| 6,258,024 B1 | * | 7/2001 | van Der Weegen | 600/115 |
| 6,402,686 B1 | * | 6/2002 | Ouchi | 600/139 |
| 6,517,477 B1 | * | 2/2003 | Wendlandt | 600/114 |
| 6,793,661 B2 | * | 9/2004 | Hamilton et al. | 606/116 |
| 2002/0143237 A1 | * | 10/2002 | Oneda et al. | 600/116 |
| 2004/0143159 A1 | | 7/2004 | Wendlandt et al. | |
| 2005/0059931 A1 | * | 3/2005 | Garrison et al. | 604/101.04 |
| 2005/0159645 A1 | * | 7/2005 | Bertolero et al. | 600/116 |
| 2007/0142706 A1 | * | 6/2007 | Matsui et al. | 600/115 |

FOREIGN PATENT DOCUMENTS

| | | |
|---|---|---|
| EP | 1 570 778 A1 | 9/2005 |
| JP | 10-127564 A | 5/1998 |
| JP | 10-137175 A | 5/1998 |
| JP | 2001-170000 A | 6/2001 |
| JP | 2004-236684 A | 8/2004 |
| JP | 2005-230083 A | 9/2005 |

OTHER PUBLICATIONS

Japanese Office Action mailed Feb. 2, 2012 with English Translation.

* cited by examiner

*Primary Examiner* — Matthew J Kasztejna
(74) *Attorney, Agent, or Firm* — Birch, Stewart, Kolasch & Birch, LLP

(57) ABSTRACT

An endoscope includes: an insert portion having a bending portion for bending operation and a flexible soft portion connected to the proximal end of the bending portion; an inflatable/deflatable balloon attached on the proximal side from the bending portion; and a supplying/sucking opening provided in the outer surface of a ring that connects the bending portion to the soft portion, the supplying/sucking opening supplying and sucking fluid to and from the balloon.

4 Claims, 3 Drawing Sheets

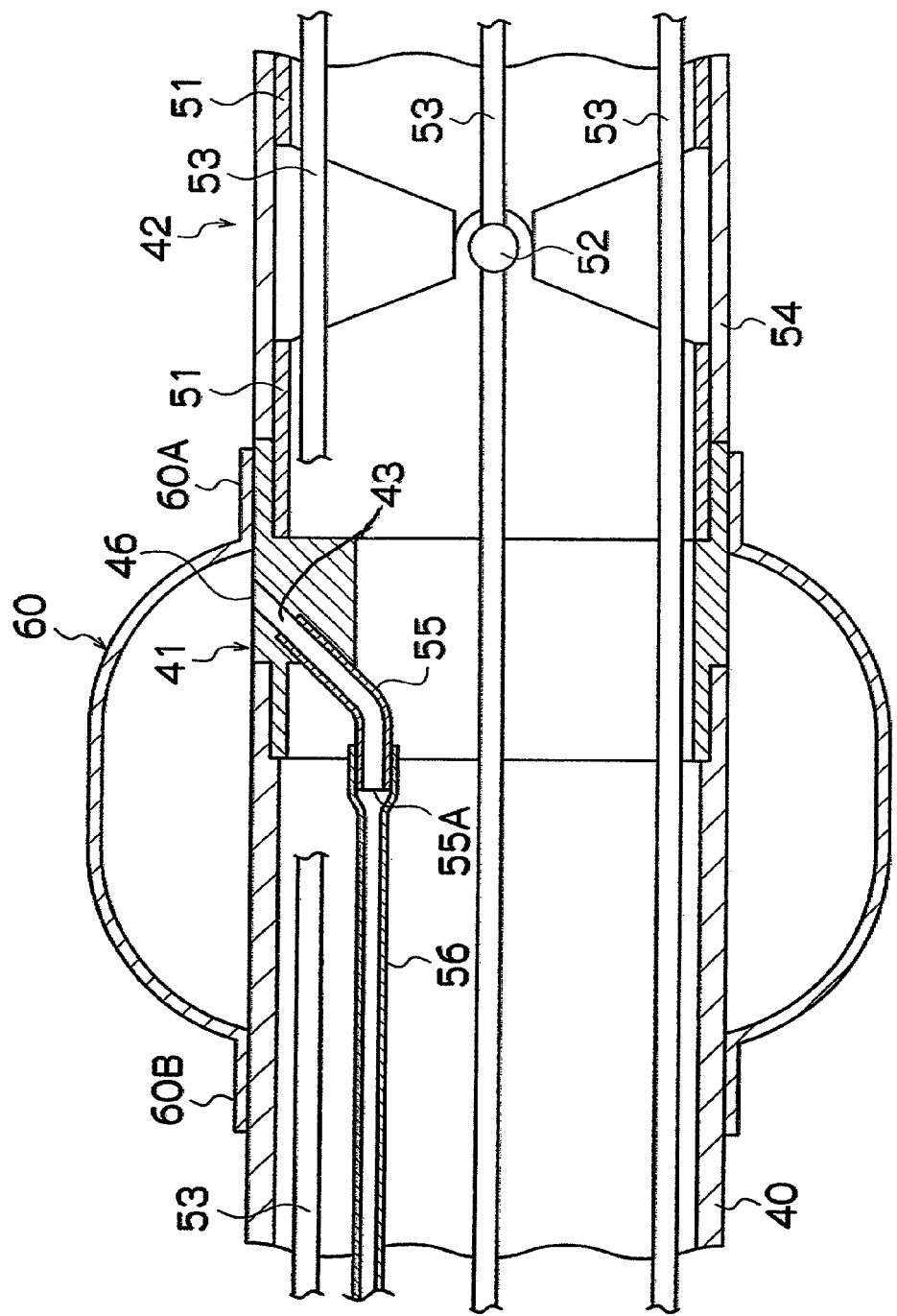

ENDOSCOPE

BACKGROUND OF THE INVENTION

1. Field of the Invention

The present invention relates to an endoscope, and particularly to an endoscope having an insert portion to be inserted into a deep digestive tract, such as small intestine and large intestine, for observation.

2. Description of the Related Art

When an insert portion of an endoscope is inserted into a deep digestive tract, such as small intestine, simply pushing the insert portion, in many cases, will not transfer the force to the tip of the insert portion because of complex bends of the intestinal tract, making deep insertion difficult. For example, when the insert portion is bent or flexed more than necessary, the insert portion cannot be inserted any deeper. To address this problem, there has been proposed a method for preventing the insert portion from being bent or flexed more than necessary by covering the insert portion of the endoscope with an insert assist tool, inserting the insert portion covered by the insert assist tool in a body cavity and using the insert assist tool to guide the insert portion.

Japanese Patent Application Laid-Open No. 2005-230083 describes an endoscope apparatus including a first balloon provided at the tip of an insert portion of the endoscope and a second balloon provided at the tip of an insert assist tool (also referred to as an overtube or a sliding tube). The first and second balloons can be inflated to secure the insert portion and the insert assist tool in the intestinal tract of the small intestine or the like. Therefore, by repeating inflation and deflation of the first and second balloons and alternately inserting the insert portion and the insert assist tool, the insert portion can be inserted deep into the intestinal tract of the small intestine or the like that bends in a complex manner.

SUMMARY OF THE INVENTION

The endoscope apparatus described in Japanese Patent Application Laid-Open No. 2005-230083 is problematic in that the balloons are attached in such a way that they overlap with a bending portion of the endoscope, so that inflating the balloons results in poor operability of the bending portion.

Although it is desired that each of the balloons is attached in such a way that it does not overlap with the bending portion of the endoscope, both ends of the balloon cannot be fixed because of a short axial length of a hard portion (hereinafter referred to as a distal end) distal from the bending portion. To attach the balloon to a soft portion proximal from the bending portion, a hard ring needs to be provided inside the soft portion so as to form an opening for supplying and sucking fluid, disadvantageously resulting in an increased number of parts and poor flexibility of the soft portion.

The present invention has been made in view of such circumstances and aims to provide an endoscope that provides not only good bending operability when the balloon is inflated but also good flexibility of the soft portion.

To achieve the above object, a first aspect of the present invention provides an endoscope including an insert portion having a bending portion for bending operation and a flexible soft portion connected to the proximal end of the bending portion, an inflatable/deflatable balloon attached on the proximal side from the bending portion, and a supplying/sucking opening provided in the outer surface of a ring that connects the bending portion to the soft portion, the supplying/sucking opening supplying and sucking fluid to and from the balloon.

According to the first aspect of the present invention, since the balloon is attached on the proximal side from the bending portion, the bending operability of the bending portion may not be compromised when the balloon is inflated. Furthermore, according to the first aspect of the present invention, since the ring that connects the bending portion to the soft portion is used to provide the opening for supplying/sucking fluid, there is no need to separately provide a ring for the supplying/sucking opening in the soft portion, so that the flexibility of the soft portion may not be compromised. Therefore, according to the first aspect of the present invention, the bending operability when the balloon is inflated can be improved and the flexibility of the soft portion can be improved.

According to the present invention, since the balloon is attached on the proximal side from the bending portion and the opening for supplying/sucking fluid is provided in the ring that connects the bending portion to the soft portion, the bending operability when the balloon is inflated can be improved and the flexibility of the soft portion can be improved.

BRIEF DESCRIPTION OF THE DRAWINGS

FIG. 3 is a cross-sectional view of the insert portion at the position where a balloon is attached.

DETAILED DESCRIPTION OF THE INVENTION

An embodiment of the endoscope according to the present invention will be described below in detail with reference to the accompanying drawings.

Figure 1:
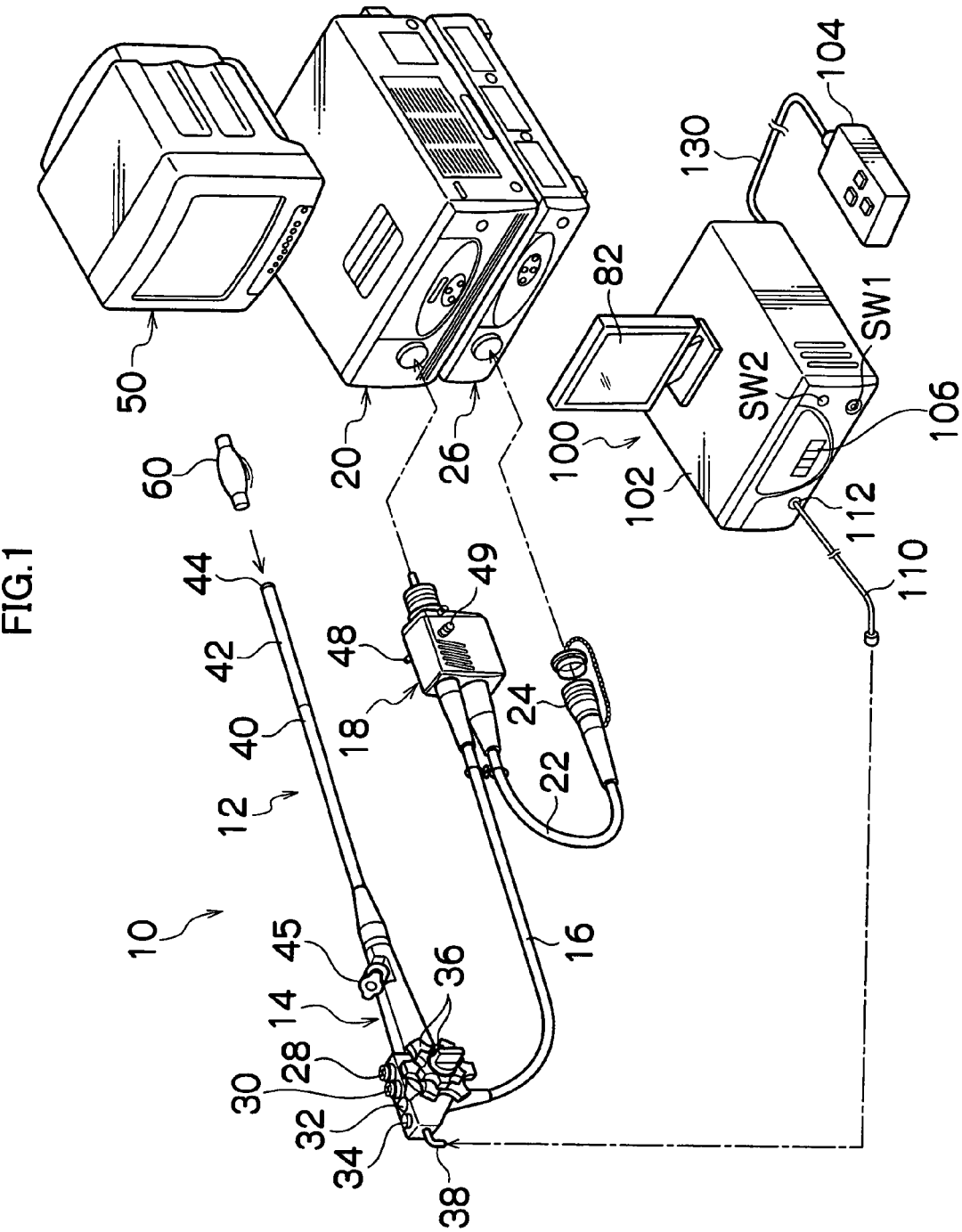
FIG. 1 is a system configuration diagram of an endoscope apparatus to which the endoscope according to the present invention is applied.

FIG. 1 is a system configuration diagram showing an example of an endoscope apparatus to which the endoscope according to the present invention is applied. As shown in FIG. 1, the endoscope apparatus primarily includes an endoscope 10 and a balloon controller 100.

The endoscope 10 includes an operator-side manipulator 14 and an insert portion 12 that is connected to the operator-side manipulator 14 and inserted into a body cavity. The operator-side manipulator 14 is connected to a universal cable 16, and an LG connector 18 is provided at the tip of the universal cable 16. The LG connector 18 is removably connected to a light source 20 in such a way that illumination light is transmitted to an illumination optical system (not shown) provided at the tip of the insert portion 12. The LG connector 18 is also connected to an electric connector 24 via a cable 22, and the electric connector 24 is removably connected to a processor 26.

The operator-side manipulator 14 not only has an air-supply/water-supply button 28, a sucking button 30, a shutter button 32 and a function switching button 34 juxtaposed but also includes a pair of angle knobs 36/36. A balloon air supply port 38 formed of an L-shaped tube is provided at the proximal end of the operator-side manipulator 14. Fluid, such as air, supplied into or sucked from the balloon air supply port 38 can inflate or deflate a balloon 60, which will be described later.

The insert portion 12 includes a soft portion 40, a bending portion 42 and a distal end 44 in this order from the operator-side manipulator 14 side. The soft portion 40 is configured such that the outer surface of a spirally wound metal plate is covered with a net and the outer surface of the net is further covered with a coating so as to provide sufficient flexibility. The soft portion 40 is connected to the proximal end of the bending portion 42 in such a way that the soft portion 40 and the bending portion 42 are connected to each other via a connection ring 41, which will be described later (see FIG. 3).

The bending portion 42 is configured to be remotely bent by pivoting the angle knobs 36/36 on the operator-side manipulator 14. For example, the bending portion 42 is configured such that a plurality of tubular node rings 51 (see FIG. 3) are pivotally connected to each other by means of guide pins 52 and a plurality of manipulation wires 53 are inserted into the node rings 51 and guided through the guide pins 52. Pushing and pulling the manipulation wires 53 pivots the node rings 51/51 with respect to each other so as to bend the bending portion 42. By bending the bending portion 42, the distal end 44 can be oriented in a desired direction.

Although the configuration of the distal end 44 is not illustrated in the drawings, for example, an observation optical system, an illumination optical system, an air-supply/water-supply nozzle and a forceps opening are provided in the front surface of the distal end 44. A CCD is disposed behind the observation optical system, and a signal cable is connected to a substrate that supports the CCD. The signal cable is inserted into the insert portion 12, the operator-side manipulator 14, the universal cable 16 and the like, extends to the electric connector 24 and is connected to the processor 26. Therefore, an image for observation acquired through the observation optical system is focused onto the light receiving surface of the CCD and converted into an electric signal. The electric signal is then outputted to the processor 26 via the signal cable and converted into an image signal. In this way, the image for observation is displayed on a monitor 50 connected to the processor 26.

The exit end of a light guide is disposed behind the illumination optical system. The light guide is inserted into the insert portion 12, the operator-side manipulator 14 and the universal cable 16, and the entrance end of the light guide is disposed in the LG connector 18. Therefore, by connecting the LG connector 18 to the light source 20, the illumination light emitted from the light source 20 is transmitted to the illumination optical system through the light guide and emitted forward from the illumination optical system.

The air-supply/water-supply nozzle communicates with a valve that is operated by the air-supply/water-supply button 28, and the valve communicates with an air-supply/water-supply connector 48 provided on the LG connector 18. The air-supply/water-supply connector 48 is connected to an air-supply/water-supply device (not shown) for supplying air and water. Therefore, by operating the air-supply/water-supply button 28, air or water can be injected out of the air-supply/water-supply nozzle toward the observation optical system.

The forceps opening communicates with a forceps insert portion 45. Therefore, by inserting a treatment tool, such as forceps, into the forceps insert portion 45, the treatment tool can be introduced out of the forceps opening. The forceps opening also communicates with a valve that is operated by the sucking button 30, and the valve is connected to a sucking connector 49 on the LG connector 18. Therefore, by connecting a sucking device (not shown) to the sucking connector 49 and using the sucking button 30 to operate the valve, a diseased portion and the like can be sucked into the forceps opening.

Figure 2:
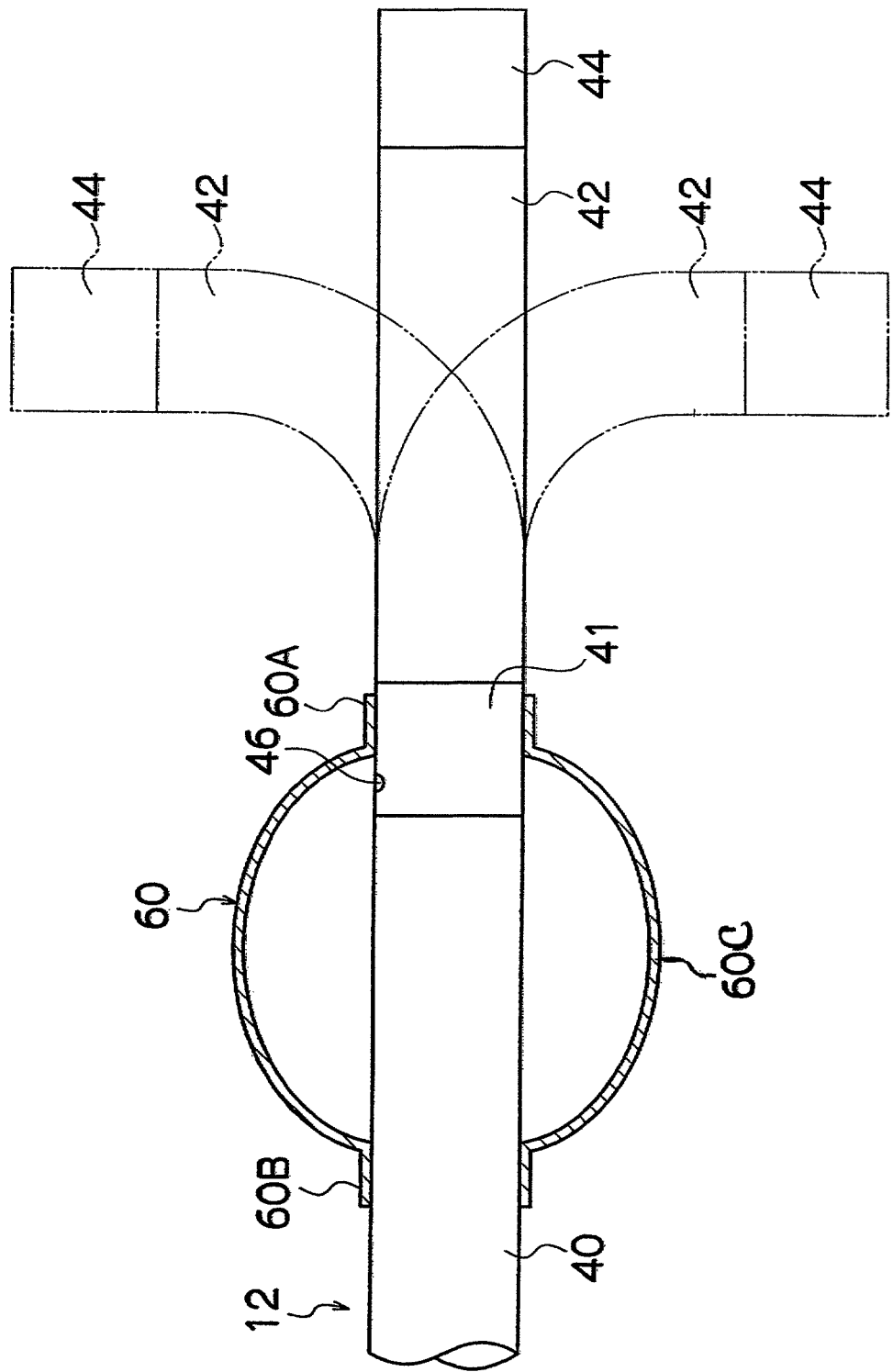
FIG. 2 is a side view showing an insert portion of the endoscope.

As shown in FIG. 2, a balloon 60 made of elastic material, such as rubber, is attached to the outer surface of the insert portion 12. The balloon 60 is formed into a substantially tubular shape having drawn ends and has small-diameter ends 60A and 60B as well as a central inflated portion 60C. After the insert portion 12 is inserted into the balloon 60 and the balloon 60 is disposed at a predetermined position (the soft portion 40) on the insert portion 12, rubber fixing rings (not shown) are fit onto the ends 60A and 60B to fix the balloon 60 to the insert portion 12. It is noted that the method for fixing the ends 60A and 60B is not limited to this specific method, but the ends 60A and 60B may be fixed by winding threads.

The balloon 60 is disposed and fixed on the proximal side from the bending portion 42. Specifically, the distal end 60A of the balloon 60 is fixed to the connection ring 41 disposed between the bending portion 42 and the soft portion 40, while the proximal end 60B is fixed to the soft portion 40.

As shown in FIG. 3, the connection ring 41 is a metal ring for connecting the most proximal node ring 51 of the bending portion 42 to the distal end of the soft portion 40. The node ring 51 of the bending portion 42 and the distal end of the soft portion 40 are fixed to the connection ring 41.

A supplying/sucking opening 46 is formed in the outer surface of the connection ring 41. The supplying/sucking opening 46 communicates with a hole 43 formed diagonally with respect to the axial direction of the connection ring 41, and the hole 43 is connected to a pipe 55. The inner portion of the connection ring 41 is thick at the position of the hole 43, allowing reliable connection to the pipe 55.

The pipe 55 is bent at some midpoint along its length. The pipe 55 is disposed such that a proximal end 55A is parallel to the axis of the connection ring 41 (longitudinal axis of the soft portion 40), and the end 55A is connected to a flexible tube 56. The tube 56 is inserted into the soft portion 40 and communicates with the balloon air supply port 38 of the operator-side manipulator 14 shown in FIG. 1. The balloon air supply port 38 is connected to the balloon controller 100 via a tube 110, which will be described later. Therefore, the balloon controller 100 can supply or suck air to inflate or deflate the balloon 60. The balloon 60 is configured such that supplying air inflates the balloon 60 into a substantially spherical shape, while sucking air allows the balloon 60 to stick on the outer surface of the insert portion 12.

The outer surface (exposed surface) of the connection ring 41 shown in FIG. 3 is coated with non-conductive material, such as fluororesin, in order to ensure safety when a high-frequency treatment tool is used. Furthermore, a circumferential groove may also be formed in the outer surface of the connection ring 41 and at the position where the end 60A of the balloon 60 is attached, so that the fixed end 60A will not project from the outer surface.

The balloon controller 100 shown in FIG. 1 is an apparatus that supplies and sucks fluid, such as air, to and from the balloon 60. The balloon controller 100 primarily includes an apparatus body 102 and a hand switch 104 for remote control.

A power supply switch SW1, a stop switch SW2 and a pressure display 106 are provided on the front side of the apparatus body 102. The pressure display 106 is a panel that displays the pressure value in the balloon 60. When the balloon 60 is under abnormal conditions, such as when the balloon is broken, the pressure display 106 displays an error code.

The tube 110 that supplies and sucks air to and from the balloon 60 is connected to the front side of the apparatus body 102. A reverse flow prevention unit 112 is provided at the portion where the tube 110 is connected to the apparatus body 102 in order to prevent a reverse flow of body fluid when the balloon 60 is broken. The reverse flow prevention unit 112 is configured by incorporating a gas-liquid separation filter in a hollow disc-shaped case (not shown) removably mounted in the apparatus body 102. The reverse flow prevention unit 112 uses the filter to prevent liquid from flowing into the apparatus body 102.

On the other hand, various switches are provided on the hand switch 104. For example, there are provided a stop switch similar to the stop switch SW2 on the apparatus body 102, an ON/OFF switch that instructs to pressurize/depressurize the balloon 60, a pause switch for maintaining the pressure in the balloon 60 and the like. The hand switch 104 is electrically connected to the apparatus body 102 via an electric cord 130. Although not shown in FIG. 1, the hand switch 104 includes a display that indicates that air has been supplied to the balloon 60 or that air has been evacuated from the balloon 60.

The thus configured balloon controller 100 supplies air to the balloon 60 to inflate it and controls the air pressure in the balloon 60 to be a fixed value so as to keep the balloon 60 inflated, while the balloon controller 100 sucks the air from the balloon 60 to deflate it and controls the air pressure in the balloon 60 to be a fixed value so as to keep the balloon 60 deflated.

The balloon controller 100 is connected to a dedicated balloon monitor 82 and displays the pressure value and the state of the balloon 60, either inflated or deflated, on the dedicated balloon monitor 82 when the balloon 60 is inflated or deflated. Alternatively, the pressure value and the state of the balloon 60, either inflated or deflated, may be displayed on the monitor 50 by superimposing the information on an image for observation acquired through the endoscope 10.

As an example of a method for operating the thus configured endoscope apparatus, the insert portion 12 is inserted by a pushing movement and the balloon 60 is inflated as required to secure the insert portion 12 in the body (such as the large intestine). Then, after the insert portion 12 is pulled to simplify the shape of a tract in the body (such as the large intestine), the balloon 60 is deflated and the insert portion 12 is inserted even deeper into the intestinal tract. For example, the insert portion 12 is inserted into the anus of the patient. When the tip of the insert portion 12 passes the sigmoid colon, the balloon 60 is inflated to secure the insert portion 12 in the intestinal tract. Then, the insert portion 12 is pulled to substantially straighten the sigmoid colon. Thereafter, the balloon 60 is deflated and the tip of the insert portion 12 is inserted deeper into the intestinal tract. In this way, the insert portion 12 can be inserted deep into the intestinal tract.

The effects of the thus configured endoscope 10 will now be described.

The balloon 60 of the endoscope 10 is configured such that the distal end 60A is fixed to the connection ring 41 and the proximal end 60B is fixed to the soft portion 40. Therefore, unlike when the end 60A or 60B of the balloon 60 is fixed on an angle rubber 54 on the bending portion 42, the angle rubber 54 may not be pressed or damaged, or the node rings 51/51 may not sandwich and damage the angle rubber 54 during bending operation. Therefore, according to this embodiment, the angle rubber 54 will not be damaged.

Furthermore, according to this embodiment, the balloon 60 is disposed on the proximal side from the bending portion 42. Therefore, as indicated by the two-dot chain lines in FIG. 2, even when the balloon 60 is inflated, the bending portion 42 can be freely bent. Therefore, according to this embodiment, bending operability can be improved when the balloon 60 is inflated.

Moreover, according to this embodiment, the connection ring 41 between the bending portion 42 and the soft portion 41 is used to form the fluid supplying/sucking opening 46. Therefore, unlike when the supplying/sucking opening 46 is provided in the soft portion 40, there is no need to newly provide a sleeve, allowing the number of parts to be reduced. Furthermore, as compared to the case where the supplying/sucking opening 46 is provided in the soft portion 40, absence of sleeve can improve the flexibility of the soft portion 40.

In the embodiment described above, although the outer surface of the connection ring 41 is coated with non-conductive material, the connection ring 41 may be covered with a cladding member and a hole is formed in the cladding member such that the hole communicates with the supplying/sucking opening 46, as far as this configuration ensures safety when a high-frequency treatment tool is used.

What is claimed is:

1. An endoscope comprising: an insert portion having a bending portion for bending operation and a flexible soft portion; a ring connected between the bending portion and the soft portion, the ring being of a hard material that is less flexible than the flexible soft portion; an inflatable/deflatable balloon in which a distal end of the balloon is at least partially attached on the ring; and a supplying/sucking opening provided in an outer surface of the ring, the supplying/sucking opening supplying and sucking fluid to and from the balloon, wherein an inner portion of the ring is formed so that a thickness of a first portion where the supplying/sucking opening portion is provided is thicker than that of a second portion other than the first portion of the ring of hard material, wherein a tube member is connected to the supplying/sucking opening at the first portion where the thickness is thicker than other portions, and wherein an end of a tip side of the balloon is fixed to the ring and an end of a proximal side of the balloon is fixed to the soft portion.

2. The endoscope according to claim 1, wherein the tube member is bent at a midpoint thereof, so that a proximal side end opposite to the supplying/sucking opening is arranged in parallel to the ring axis, and wherein the proximal side end of the tube member has a flexible tube connected.

3. An endoscope comprising: a bending portion for bending operation; a flexible soft portion; a metal ring; an inflatable/deflatable balloon in which a distal end is attached on the metal ring; and the metal ring connected between the bending portion and the flexible soft portion for connecting the bending portion to the flexible soft portion, the ring having a supplying/sucking opening provided in an outer surface thereof for supplying and sucking fluid to and from the inflatable/deflatable balloon, wherein an inner portion of the ring is formed so that a thickness of a first portion where the supplying/sucking opening portion is provided is thicker than that of a second portion other than the first portion of the metal ring, and wherein a tube member is connected to the supplying/sucking opening at the first portion where the thickness is thicker than other portions, and wherein an end of the balloon closer to the bending portion is fixed to the metal ring, and an end of the balloon closer to the flexible soft portion is fixed to the flexible soft portion.

4. The endoscope according to claim 3, wherein the tube member is bent at a midpoint thereof, so that a proximal side end opposite to the supplying/sucking opening is arranged in parallel to the ring axis, and wherein the proximal side end of the tube member has a flexible tube connected.

* * * * *